(12) United States Patent
Lohri et al.

(10) Patent No.: US 6,274,735 B1
(45) Date of Patent: Aug. 14, 2001

(54) PROCESS AND INTERMEDIATES FOR PREPARATION OF SUBSTITUTED PIPERIDINES

(75) Inventors: Bruno Lohri, Reinach; Rudolf Schmid, Basel; Eric Vieira, Allschwil, all of (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/345,917

(22) Filed: Jul. 1, 1999

(30) Foreign Application Priority Data

Aug. 10, 1998 (EP) .................................. 98114974

(51) Int. Cl.$^7$ ............................................. C07D 211/40
(52) U.S. Cl. ................................................. 546/216
(58) Field of Search ............................... 546/216

(56) References Cited

U.S. PATENT DOCUMENTS 4,132,710 * 1/1979 Gauthier et al. ....................... 546/63

FOREIGN PATENT DOCUMENTS

WO 97/09311    3/1997 (WO) .

OTHER PUBLICATIONS

C.S. Swindell et al., Heterocycles, 24(12):3373–3377 (1986).
R.F. Borne et al., J. Heterocyclic Chem., 17(7):1609–1611 (Nov. 1980).
G.A. Rogers et al., J. Med. Chem., 32(6):1217–1230 (1989).
K. Freter et al., J. Heterocyclic Chem., 19(2):377–379 (1982).
R.G. Naik et al., Tetrahedron, 44(7):2081–2086 (1988).
J.C. Jaen et al., J. Heterocyclic Chem., 24:1317–1319 (1987).
D.E. Bays et al., J. Chem. Soc. Perkin Trans. 1, 1187–1200 (1989).
M.A. Iorio et al., Eur. J. Med. Chem.—Chimica Therapeutica, 15(2):165–172 (1980).
H. C. Brown et al., J. Org. Chem., 52:310–311 (1987).
C. E. Kaslow et al., J. Am. Chem. Soc., 77:1054–1055 (1955).
Abstract, WPI Acc. No. 97–201899/199718 (Abstract of WO 97/09311).
Biswas et al. "Diborane as a reducing agent . . . " Ca 66:18423, 1966.*
Vit et al. "Agent for preparation of diborane by . . . " CA 75:142401, 1964.*
Jaworski et al. "Diboron hexahydride" CA 99:142474, 1979.*

* cited by examiner

Primary Examiner—Ceila Chang
(74) Attorney, Agent, or Firm—George W. Johnston; Patricia S. Rocha-Tramaloni; Eileen M. Ebel

(57) ABSTRACT

The present invention concerns intermediates useful in and a process for the preparation of a compound of formula 1 or a salt thereof

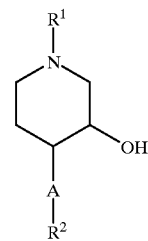

1 comprising a) hydroboration of a compound of formula 2

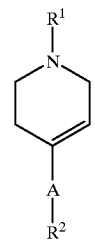

2

A, $R^1$ and $R^2$ are as herein defined. These compounds are useful in the synthesis of renin inhibitors.

16 Claims, No Drawings

PROCESS AND INTERMEDIATES FOR PREPARATION OF SUBSTITUTED PIPERIDINES

SUMMARY OF THE INVENTION

The invention relates to novel intermediates useful in and a novel process for the preparation of substituted piperidines. More particularly, the invention relates to the preparation of compounds of the formula 1

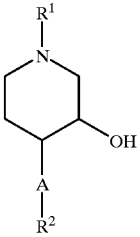

1 and salts thereof, wherein

A is arylene;
$R^1$ is —$C^*R^3R^4R^5$;
$R^2$ is —O-alkyl, —O-cycloakyl, —O-alkenyl, —O-aryl, —O-aralkyl, —O-aralkoxyalkyl, —O-alkylsulfonyl, —O-arylsulfonyl, chlorine, bromine or iodine;
$R^3$ hydrogen;
$R^4$ is aryl;
$R^5$ is alkyl, cycloalkyl, aryl, alkoxyalkyl or hydroxyalkyl;
and $C^*$ is an asymmetric carbon atom.

The invention also relates to novel compounds of formula 1 which are useful as chiral building blocks in the preparation of renin inhibitors, especially disubstituted renin inhibitors as is disclosed in WO 97109311 e.g. 1-[2-[7-[(3R,4R)-4-[4-[3-(2-methoxy-benzyloxy)-propoxy]-phenyl]-piperidin-3-yloxymethyl]-naphthalen-2-yloxy]-ethyl]-4-methyl-piperazine and (3R,4R)-4-[4-[3-(2-methoxy-benzyloxy)-propoxy]-phenyl]-3-(1,2,3,4-tetrahydro-quinolin-7-ylmethoxy)-piperidine.

BACKGROUND OF THE INVENTION

The syntheses of optically active renin inhibitors via conventional resolution of racemates as disclosed in WO 97/09311 results in a considerable loss of product. The present invention provides a novel process which avoids the disadvantages of the foregoing process.

DETAILED DESCRIPTION OF THE INVENTION

According to the present invention, compounds of formula 1 above and their salts can be prepared by a process comprising:

a) hydroboration of a compound of formula 2

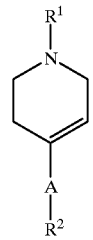

2 wherein
$R^1$, $R^2$ and A are defined as above.

In another embodiment of the present invention, Step a) above may be optionally followed by isolation of the desired stereoisomer.

The term "alkyl" means alone or in combination a branched or unbranched alkyl group containing 1 to 8 carbon atoms, preferred 1 to 6 carbon atoms. Examples for branched or unbranched $C_1$–$C_8$ alkyl groups are methyl, ethyl, propyl, isopropyl, butyl, isobutyl, tert-butyl, the isomeric pentyls, the isomeric hexyls, the isomeric heptyls, the isomeric octyls and preferred ethyl, n-propyl, and isopropyl and particularly preferred methyl.

The term "cycloalkyl" means alone or in combination a cycloalkyl cycle with 3 to 8 carbon atoms and preferred a cycloalkyl cycle with 3 to 6 carbon atoms. Examples for $C_3$–$C_8$ cycloalkyl are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl and cycloheptyl.

The term "alkenyl" means alone or in combination alkenyl groups of 2 to 8 carbon atoms. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-ethyl-2-butenyl, and the like. Preferred is allyl.

The term "aryl" means alone or in combination a phenyl or a naphthyl group which can be substituted by one or several substituents chosen from alkyl, cycloalkyl, alkoxy, halogen, carboxy, alkoxycarbonyl, hydroxy, amino, nitro, trifluoromethyl and the like. Example of aryl substituents are phenyl, tolyl, methoxyphenyl, fluorophenyl, chlorophenyl, hydroxyphenyl, trifluoromethylphenyl, 1-naphthyl and 2-naphthyl.

The term "arylene" means alone or in combination a phenylene or a naphthylene group which optionally can be substituted by one or several substituents chosen from alkyl, halogen, nitro, cycloalkyl, alkoxy, hydroxy, amino, preferably alkyl, halogen and nitro. Examples for arylene are ortho-phenylene, meta-phenylene, para-phenylene, the tolylenes, methoxyphenylenes, fluorophenylenes, chlorophenylenes and naphthylenes. Preferred are phenylene, wherein the substituents of the phenylene which are defined by formula 1 are placed ortho, meta or preferred para to one another and wherein one or several additional substituents chosen from alkyl, halogen and nitro can be present at the arylene cyclus. Especially preferred substituents are methyl, chloro and nitro. Particularly preferred is unsubstituted phenylene and especially unsubstituted para phenylene.

The term "alkoxy" means alone or in combination the group —O-alkyl, wherein alkyl is defined as before. Examples are ethoxy, n-propyloxy, and iso-propyloxy. Preferred is methoxy.

The term "alkoxyalkyl" means alone or in combination an alkyl group, wherein a hydrogen is substituted by an alkoxy group. Examples are methoxymethyl, ethoxymethyl and 2-methoxyethyl. Particular preferred is methoxymethyl.

The term "aralkyl" means alone or in combination an alkyl group, wherein a hydrogen is substituted by an aryl group. A preferred example is benzyl.

The term "hydroxyalkyl" means alone or in combination an alkyl group, wherein a hydrogen is substituted by an hydroxy group. Examples are hydroxymethyl, 1-hydroxyethyl and 2-hydroxyethyl. Preferred is hydroxymethyl.

The term "aralkoxyalkyl" means alone or in combination an alkyl group, wherein a hydrogen is substituted by an alkoxy group in which a hydrogen is substituted by an aryl group. A preferred example for aralkoxyalkyl is 3-(2-methoxy-benzyloxy)-propyl.

The term "alkylsulfonyl" means alone or in combination a sulfonyl group which is substituted by an alkyl group. The alkyl group can be substituted by halogen. Preferred examples are methylsulfonyl and trifluoromethylsulfonyl.

The term "arylsulfonyl" means alone or in combination a sulfonyl group which is substituted by an aryl group. Preferred is the tosyl group.

The term "salts" means compounds which are formed by reaction of compounds of formula 1 with inorganic acids such as hydrochloric acid, hydrobromic acid, sulfuric acid, nitric acid, phosphoric acid, and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. The term salts includes solvates and particularly hydrates of such salts.

The term "halogen" means fluorine, chlorine, bromine, iodine and preferably chlorine and bromine. Most preferred is chlorine.

The term "anion" means an atom, a group of atoms or a molecule with negative charge. This charge can be a single or a multiple charge. Examples of anions are the halogen anions, $SO_4^{2-}$, $PO_4^{3-}$. Particularly preferred is the Cl-anion.

The term "asymmetric carbon atom (C*)" means a carbon atom with four different substituents. According to the Cahn-Ingold-Prelog-Convention, the asymmetric carbon atom can have "R" or "S" configuration. A preferred example for an asymmetric carbon atom (C*) is shown in the formula

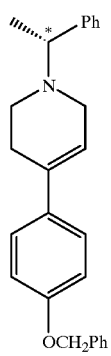

wherein the asymmetric carbon atom C* is of the R configuration.

The term "—O—" in groups such as —O-alkyl, —O-cycloalkyl, —O-alkenyl, —O -aryl, —O-benzyl, —O-aralkoxyalkyl, —O-alkylsulfonyl, —O-arylsulfonyl, means an oxygen with a free valence. For example —O-alkyl means alkoxy and —O -cycloalkyl means cycloalkoxy.

In a preferred embodiment, the above process is used to prepare compounds of the formula 1 wherein $R^5$ is alkyl or cycloalkyl and $R^1$, $R^2$ and A are defined as above.

Also preferred is a process according to the present invention, wherein $R^4$ is unsubstituted phenyl or substituted phenyl and, wherein the substituents of phenyl are independently selected from one or more alkyl, halogen or nitro, preferably methyl or chloro. In a particularly preferred embodiment of the above process, $R^4$ is unsubstituted phenyl and $R^1$, $R^2$ and A are defined as above, preferably, wherein $R^5$ is alkyl, most preferably methyl.

Particularly preferred is the process above wherein $R^4$ is phenyl, $R^5$ is methyl, and $R^1$, $R^2$ and A are as otherwise defined supra.

In another preferred embodiment of the present invention, A is substituted or unsubstituted ortho, meta or para phenylene. When substituted, the substituents on the phenylene are placed ortho, meta or para to one another. The para position is preferred. The substituted phenylene has one or several substituents chosen from alkyl, halogen and nitro. Most preferably, A is unsubstituted phenylene, and in particular unsubstituted para phenylene.

In another preferred embodiment of the present invention, $R^2$ is selected from —O-alkyl, —O-cycloalkyl, —O-aryl, —O-benzyl or —O-aralkyl. Preferably $R^2$ is selected from —O-benzyl and —O-methyl. Most preferred $R^2$ is —O-benzyl.

Hydroboration is effected by any hydroboration reaction known to one skilled in the art. For example hydroboration of a compound of formula 2 may be effected by use of a chiral or achiral hydroboration reagent. Preferred examples of useful hydroboration reagents include $NaBH_4/BF_3.Et_2O$, $BH_3$-THF, $BH_3$-dimethylsulfide complex, $BH_3$-triethylamine complex, 9-borabicyclo(3.3.1)-nonane, isopinocampheyl-borane, or a chemical equivalent of any of the mentioned reagents. In a particularly preferred process according to the invention, a compound of formula 2 is reacted with $NaBH_4/BF_3.Et_2O$, $BH_3$ -THF or isopinocampheyl borane. Preferrably, the hydroboration agent is selected from are $NaBH_4/BF_3.Et_2O$ and isopinocampheyl borane.

Compounds of formula 2 above and their salts are new and also form a part of the present invention.

Compounds of formula 2 may be obtained by reacting a compound of formula 3 or 4

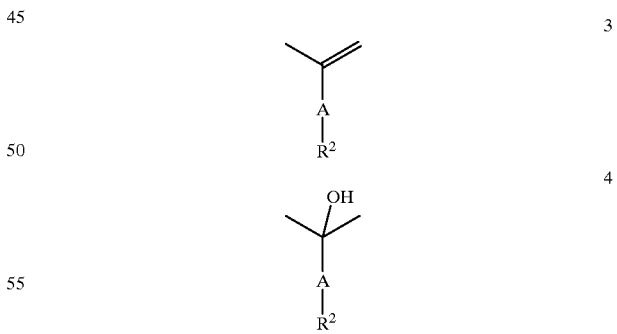

with a compound of formula $R^1$—$NH_2$ or a salt thereof, wherein $R^1$, $R^2$ and A have the same meanings as given above. Preferably, this reaction is effected in the presence of formaldehyde (a reactant) or a compound which forms formaldehyde during the above reaction (hereinafter referred to as a "chemical equivalent" thereof).

Preferred compounds of formula 2 include (R)-4-(4-benzyloxy-phenyl)-1-(1-phenyl-ethyl)-1,2,3,6-tetrahydro-pyridine and salts thereof.

Another preferred aspect of the present invention is the isolation of the desired stereoisomer of a compound of formula 1 by crystallisation of a salt of said compound. Particularly preferred is the crystallisation of a chloride of a compound of the formula 1. Crystallization of salts of compounds of formula 1 is accomplished by methods known to those skilled in the art.

In another embodiment of the present invention, the above process is followed by a reaction with hydrogen. A particularly preferred embodiment is the reaction of a compound of the formula 1 or a salt thereof, preferably the desired stereoisomer of a compound of the formula 1 or a salt thereof, with hydrogen, most preferably in the presence of a catalyst such as palladium on carbon.

Another preferred aspect of the present invention is the transformation of (3R,4R)-4-(4-benzyloxy-phenyl)-1-((R)-1-phenyl-ethyl)-piperidin-3-ol hydrochloride to 1-[2-[7-[(3R,4R)-4-[4-[3-(2-methoxy-benzyloxy)-propoxy]-phenyl]-piperidin-3-yloxymethyl]-naphthalen-2-yloxy]-ethyl]-4-methyl-piperazine by the following procedure: a) reacting (3R,4R)-4-(4-benzyloxy-phenyl)-1-((R)-1-phenyl-ethyl)-piperidin-3-ol hydrochloride with hydrogen to yield (3R,4R)-4-(4-hydroxy-phenyl)-piperidin-3-ol hydrochloride;

b) reacting the product of step a) with di-tert.-butyl-dicarbonate in the presence of a base to form (3R,4R)-3-hydroxy-4-(4-hydroxy-phenyl)-piperidin-1-carboxylic-acid-tert-butylester;

c) reacting the product of step b) with 1-(3-chloro-propoxymethyl)-2-methoxy-benzene and potassium carbonate to yield (3R,4R)-3-hydroxy-4-[4-[3-(2-methoxy-benzyloxy)-propoxy]-phenyl]-piperidine-1-carboxylic acid tert-butylester;

d) reacting the product of step c) with 2-chloromethyl-7-(2-trimethylsilanyl-ethoxymethoxy)-naphthalene and sodium hydride to form (3R,4R)-4-[4-[3-(2-methoxy-benzyloxy)-propoxy]-phenyl]-3-[7-(2-trimethyl-silanyl-ethoxymethoxy)-naphthalen-2-ylmethoxy]-piperidine-1-carboxylic acid tert-butylester;

e) reacting the product of step d) with hydrochloric acid to yield (3R,4R)-3-(7-hydroxy-naphthalen-2-yloxymethyl)-4-[4-[3-(2-methoxy-benzyloxy)-propoxy]-phenyl]-piperidine-1-carboxylic acid tert-butylester;

f) reacting the product of step e) with 1-(2-hydroxy-ethyl)-4-methyl-piperazine and triphenylphosphine to yield (3R,4R)-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidine-1-carboxylic acid tert-butylester; and g) reacting the product of step f) with hydrogen chloride.

Also preferred is the transformation of (3R,4R)-4-(4-benzyloxy-phenyl)-1-((R)-1-phenyl-ethyl)-piperidin-3-ol hydrochloride to (3R,4R)-4-[4-[3-(2-methoxy-benzyloxy)-propoxy]-phenyl]-3-(1,2,3,4-tetrahydro-quinolin-7-ylmethoxy)-piperidine by the following procedure:

a) reacting (3R,4R)-4-(4-benzyloxy-phenyl)-1-((R)-1-phenyl-ethyl)-piperidin-3-ol hydrochloride with hydrogen to yield (3R,4R)-4-(4-hydroxy-phenyl)-piperidin-3-ol hydrochloride;

b) reacting the product of step a) with di-tert-butyl-dicarbonate in the presence of a base to form (3R,4R)-3-hydroxy-4-(4-hydroxy-phenyl)-piperidin-1-carboxylic-acid-tert-butylester;

c) reacting the product of step b) with 1-(3-chloro-propoxymethyl)-2-methoxy-benzene and potassium carbonate to yield (3R,4R)-3-hydroxy-4-[4-[3-(2-methoxy-benzyloxy)-propoxy]-phenyl]-piperidine-1-carboxylic acid tert-butylester;

d) reacting the product of step c) with 7-bromomethyl-quinoline hydrobromide and sodium hydride to yield (3R,4R)-4-[4-[3-(2-methoxy-benzyloxy)-propoxy]-phenyl]-3-(quinolin-7-yl-methoxy)-piperidine-1-carboxylic acid tert-butylester;

e) reacting the product of step d) with sodium borohydride to yield (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester; and f) reacting the product of step e) with hydrochloric acid.

The present invention is also directed to compounds of formula 1:

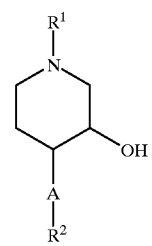

1 wherein
R¹, R² and A are defined as above, and to salts of these compounds.

Preferred compounds of formula 1 include (3R,4R)-4-(4-benzyloxy-phenyl)-1-((R)-1-phenyl-ethyl)-piperidin-3-ol and salts thereof.

Furthermore, compounds of the formula 5 and their salts are also a part of the present invention:

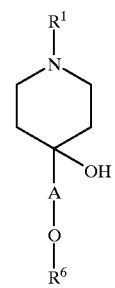

5 wherein
R¹ and A are defined as above and R⁶ is alkyl, cycloalkyl, alkenyl, aryl, aralkyl, aralkoxyalkyl, alkylsulfonyl or arylsulfonyl.

Particularly preferred compounds of formula 5 include (R)-4-(4-benzyloxy-phenyl)-1-(1-phenyl-ethyl)-piperidin-4-ol and salts thereof.

The invention also relates to the use of a compound of formula 1 in the preparation of renin inhibitors, preferably in the preparation of 1-[2-[7-[(3R,4R)-4-[4-[3-(2-methoxy-benzyloxy)-propoxy]-phenyl]-piperidin-3-yloxymethyl]-naphthalen-2-yloxy]-ethyl]-4-methyl-piperazine and (3R,4R)-4-[4-[3-(2-methoxy-benzyloxy)-propoxy]-phenyl]-3-(1,2,3,4-tetrahydro-quinolin-7-ylmethoxy)-piperidine.

Furthermore, the invention also relates to compounds as obtained by the above-described process.

More specifically, the process of the invention may be described as follows:
Hydroboration of a compound of formula 2 and optionally isolation of the desired stereoisomer:

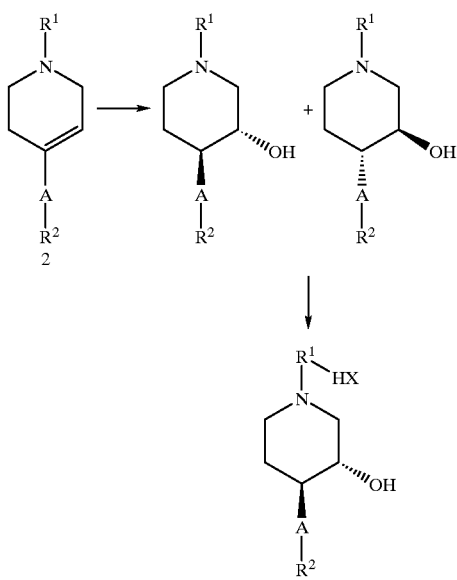

wherein
$R^1$, $R^2$, A are defined as before and X is an anion, preferably Cl—.

A compound of the formula 2 can be reacted with compounds which are known for use in hydroboration reactions and especially with chiral or achiral hydroboration reagents using inert solvents. Examples for such reagents are $BH_3$-THF, $BH_3$-dimethylsulfide complex, $BH_3$-triethylamine complex and 9-borabicyclo(3.3.1)-nonane or a chemical equivalent of anyone of the mentioned compounds. Preferred are isopinocampheylborane and particularly preferred is $NaBH_4/BF_3\cdot Et_2O$. Also included are chemical equivalents of anyone of these compounds. Inert solvents taken alone or in combination can be used, particularly, solvents which are known for their utilisation in hydroboration reactions. Examples of such solvents are linear or cyclic ethers such as dimethylether, diethylether, tetrahydrofuran, dioxane, monoglyme, diglyme and mixtures of any of these solvents. A preferred solvent is dimethoxyethane.

A temperature range of from about –20° C. to the boiling point of the solvent is suitable for the reaction of the present invention. The preferred temperature range is between about –20° C. to about 20° C. preferably from about 0° C. to about 5° C.

The above reaction is followed by an oxidative work-up under basic conditions including addition of a base such as NaOH and an oxidising agent, for example perborate or preferably $H_2O_2$.

The temperature range for the addition of the base and the oxidising agent is from about –20° C. to the boiling point of the solvent. A preferred temperature range for the addition of the base is from about 0° C. to about 10° C., and most preferably from about 5° C. to about 10° C. The reaction mixture is treated with the oxidising agent preferably at temperatures ranging from about 20° C. to about 60° C., and most preferably from 30–50° C. However, lower or higher temperatures also may be used.

According to the above process compounds of formula 1 may be formed as a mixture of stereoisomers, preferably a mixture of diastereomers. It is also possible that only one of the diastereomers is formed by the above process. In a preferred embodiment of the described process, only one of the diastereomers is formed.

In a preferred embodiment of the invention (R)-4-(4-benzyloxy-phenyl)-1-(1-phenyl-ethyl)-1,2,3,6-tetrahydropyridine yields a mixture of (3R,4R)-4-(4-benzyloxy-phenyl)-1-((R)-1-phenyl-ethyl)-piperidin-3-ol and (3S,4S)-4-(4 -benzyloxy-phenyl)-1-((R)-1-phenyl-ethyl)-piperidin-3-ol, most preferably the products are formed in a ratio of about 3:1.

Optionally, the desired diastereomer can be isolated by methods known in the art such as crystallisation, chromatography or distillation. These methods also include the formation of salts or derivatives of compounds of the formula 1 followed by separation of these salts or derivatives by crystallisation, chromatography, distillation, etc. These methods for the separation of diastereoismers are well known in the art and are for example described in Houben-Weyl, Methods of Organic Chemistry (Thieme 1952).

A preferred method of isolation of a particular diastereomer from a -mixture that includes both diasteromers is the crystallisation of the salts of compounds of formula 1. Especially preferred acids which can be used for the formation of salts of compounds of the formula 1 include hydrohalic acids, preferably HCl.

Preferred solvents which can be used for the crystallisation of compounds of formula 1, in particular the crystallization of of salts of compounds of formula 1, are protic or aprotic solvents that do not react with compounds of formula 1. Particularly preferred solvents include ethanol, methanol or their mixtures with pentane or hexane.

One preferred embodiment of the isolation of the desired stereoisomer according to the invention is the crystallisation of hydrochlorides of compounds of formula 1 in solvents such as ethanol, isopropanol, or preferably methanol.

After isolation the desired stereoisomer, preferably diastereomer, can be reacted with hydrogen, preferably in the presence of a catalyst such as palladium on carbon or any other catalyst which is suitable in the hydrogenolytic removal of groups such as benzyl. Preferred solvents for this reaction are, for example, alcohols, water or acetic acid either alone or in combination. Particularly preferred is the mixture of methanol and water. The resulting compound can then be transformed by reaction with di-tert-butyl-dicarbonate, preferably in the presence of a base such as triethylamine. A preferred solvent for this reaction is, for example, methanol. The resulting compound can then be used in the preparation of renin inhibitors as is disclosed in WO 97/09311.

In general, the above-resulting compounds may be used in the preparation of renin inhibitors as follows. The selective functionalization of the phenolic function can be performed with alkylation reactions using aliphatic or benzylic chlorides, bromides, iodides, tosylates or mesylates in the presence of a base like potassium carbonate in solvents such as an ether like tetrahydrofuran, dimethylformamide, dimethylsulfoxide, acetone, methyl-ethyl-ketone, or pyridine at temperatures between 0° C. and 140° C. The alkylating agents used can either contain the whole chain desired to be included or optionally can be suitably protected by functional groups which allow further structural modifications at a later stage of the synthesis. Functionalization at the secondary hydroxy function of the piperidine ring can then be performed in solvents as ethers like tetrahydrofuran or 1,2-dimethoxyethane, or in dimethylformamide or dimethylsulfoxide in the presence of a base like sodium hydride or potassium tert-butoxide and a suitable alkylating agent, preferentially an aryl methyl chloride, bromide, mesylate or tosylate at temperatures between 0° C. and 40° C. Again, the alkylating agents used can either contain the whole substituent desired or optionally can be suitably protected by functional groups which allow further structural modifications at a later stage of the synthesis. Further structural variations can comprise removal of protective functions followed by functionalization of the liberated functional groups, e.g. etherification of a phenolic moiety. Reduction may also be used, such as of a quinoline unit to a tetrahydroquinoline unit by, for example, sodium borohydride or nickel chloride in solvents such as methanol or ethanol. Final removal of the Boc-protective group can be performed in the presence of acids such as hydrochloric, hydrobromic, sulfuric, phosphoric, trifluoroacetic acid in a variety of solvents such as alcohols and alcohol/water mixtures, ethers and chlorinated hydrocarbons. The Boc-protective group can also be removed with anhydrous zinc bromide in inert solvents such as dichloromethane.

Compounds of formula 2 can be prepared as follows:

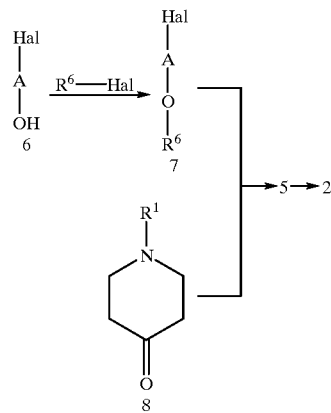

Compound 5 is reacted with an acid, e.g. oxalic acid in an inert solvent to form a compound of formula 2. Compound 5 is formed by reacting a compound of the formula 7 in an inert solvent with butyllithium or a Grignard reagent to form an organometallic intermediate which is reacted with a compound of the formula 8. Compound 7 can be obtained by reacting a compound of formula 6 with a compound of the formula $R^6$-Hal in the presence of a base and preferably a catalyst such as NaI in an inert solvent. $R^6$ is alkyl, cycloalkyl, alkenyl, aryl, aralkyl, aralkoxyalkyl, alkylsulfonyl or arylsulfonyl. Compound 8 can be obtained by the reaction of $R^1$-$NH_2$ with 1-ethyl-1-methyl-4-oxo-piperidinium iodide in the present of a base. 1-Ethyl-1-methyl-4-oxo-piperidinium iodide can be obtained by the reaction of 1-ethyl-4-piperidone with methyl iodide in an inert solvent.

Alternatively, as was discussed earlier, a compound of formula 2 can be obtained by the reaction of an ammonium salt having the formula $R^1$—$NH_3^+X^-$ with formaldehyde and a compound of formula 3. Compounds of formula 3 can be obtained, for example, by a Wittig reaction of the appropriate phosphorane with a compound of formula 9 in the presence of an inert solvent.

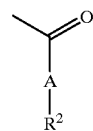

Alternatively, compounds of formula 2 can be prepared by the reaction of an ammonium salt of the formula $R^1$—$NH_3^+$ $X^-$ with formaldehyde and with a compound of the formula 4. Compounds of formula 4 can be prepared by the reaction of an organometallic compound containing a methyl group attached to the metal as in methylmagnesium bromide or methyllithium, with compound 9. Compounds of formula 4 wherein $R^2$ is chlorine, bromine or iodine can be prepared via oxidation of a halocumene (for example as described in U.S. Pat. No. 3,954,876 or DE 2302751).

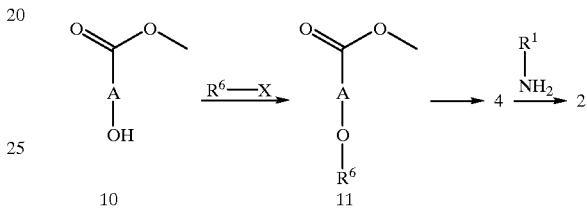

Alternatively, compounds of formula 2 can be prepared by reacting a salt of the formula $R^1$—$NH_3X$ with formaldehyde and a compound of formula 4. Preferably, $R^1$—$NH_3X$ is generated in the reaction mixture from a compound $R^1$—$NH_2$ using the appropriate amount of a suitable acid HX. Furthermore, a compound of formula 4 can be obtained by the reaction of a compound of formula 11 with an appropriate organometallic compound. Compound 11 can be prepared by reacting a compound of formula 10 with $R^6$-X in the presence of a base in an inert solvent. $R^6$ has the meaning given as above.

The following preparations and examples illustrate preferred embodiments of the present invention but are not intended to limit the scope of the invention.

EXAMPLE 1

Preparation of Product
a) Preparation of (3R,4R)-4-(4-benzyloxy-phenyl)-1-((R)-1-phenyl-ethyl)-piperidin-3-ol The reaction flask was charged under argon with 60 g (162 mmol) of (R)-4-(4-benzyloxy-phenyl)-1-(1-phenyl-ethyl)-1,2,3,6-tetrahydro-pyridine and 600 mL of dimethoxyethane. After addition of 9.2 g (243 mmol) of sodium-borohydride the mixture was cooled to 0° C. under stirring. Then 45.9 g (323 mmol) of borontrifluoride-diethyletherate was added during 40 min, wherein the temperature was kept at 0–5° C. The reaction mixture was stirred at 5° C. for additional 2 h and then at room temperature for 165 min. After cooling to 0° C., 350 mL of 4 N NaOH was added during 1 h, wherein the temperature was kept at 5–10° C. Then 60 mL of 30% $H_2O_2$ was added at 20° C. during 1 h. After additional stirring for 20 min the mixture was heated to 45° C., which caused the temperature to raise temporarily to 55° C. After cooling, the temperature was kept at 45° C. for a total of 3 h. After stirring overnight at room temperature the reaction mixture was poured into a mixture of 1 L half-saturated NaCl solution and 800 mL of ethyl acetate. After extraction with ethyl acetate the organic phases were washed with water and dried over Na$_2$SO$_4$. After concentration, 67.4 g of the diastereomeric mixture of (3R,4R)-4-(4-benzyloxy-phenyl)-1-((R)-1-phenyl-ethyl)-piperidin-3-ol and (3S,4S)-4-(4-benzyloxy-phenyl)-1-((R)-1-phenyl-ethyl)-piperidin-3-ol were obtained in a ratio of 3:1.

b) Isolation of (3R,4R)-4-(4-benzyloxy-phenyl)-1-((R)-1-phenyl-ethyl)-piperidin-3-ol-hydrochloride 25 mL of 37% HCl were added over 30 min to 80 mL of ethanol at 5° C. This mixture was added under stirring at 15° C. during 1 h to a solution of 67.4 g of the product mixture obtained by reaction a) in 300 mL of ethyl acetate. Crystals began to form after addition of ⅓ of the above ethanolic/HCl solution. The mixture was stirred for 4 h at 0° C. and then 100 mL of pentane was added and stirring was continued for 1 h at 0° C. The crystals were separated, washed with pentane (2×50 mL) and dried in vacuo. 61.5 g of crude hydrochlorides of the diastereomeric alcohols was obtained. The hydrochlorides were dissolved at 60° C. in 260 mL methanol and were crystallised overnight under stirring and cooling down to room temperature. The crystals were separated, washed with ethanol (2×50 mL) and pentane (2×80 mL) and dried in vacuo to yield 38.3 g of (3R,4R)-4-(4-benzyloxy-phenyl)-1-((R)-1-phenyl-ethyl)-piperidin-3-ol-hydrochloride as white crystals.

EXAMPLE 2

Preparation of Product a) Preparation of (3R,4R)-4-(4-benzyloxy-phenyl)-1-((R)-1-phenyl-ethyl)-piperidin-3-ol The reaction flask was charged under argon with 4 mL of a 0.75 M solution of isopinocampheyl-borane (IpcBH$_2$ derived from (+)-α-pinene) in THF. 1 mmol of (R)-4-(4-benzyloxy-phenyl)-1-(1-phenyl-ethyl)-1,2,3,6-tetrahydropyridine was added and the mixture was stirred for 16 h at 22° C. The work-up of the reaction mixture included treatment with acetaldehyde and alkaline H$_2$O$_2$ and was carried out in analogy to the method described by H. C. Brown et al. (*J. Org. Chem.* 1987, 52, 310) for this type of hydroboration. Chromatography of the crude product afforded 240 mg of a mixture of (3R,4R)-4-(4-benzyloxy-phenyl)-1-((R)-1-phenyl-ethyl)-piperidin-3-ol and (3S,4S)-4-(4-benzyloxy-phenyl)-1-((R)-1-phenyl-ethyl)-piperidin-3-ol in a ratio of 85:15.

b) Separation of the Desired Stereoisomer can be Performed as Described in Example 1b).

EXAMPLE 3

Preparation of Starting Material a) Preparation of 4-benzyloxybromobenzene 200 g (1.16 mol) of 4-bromophenol was dissolved in 2.1 L acetone under argon. Then 320 g (2.31 mol) K$_2$CO$_3$ and 3.465 g (23.1 mmol) NaI were added. The mixture was stirred at room temperature and 292.7 g (2.31 mol) of benzyl chloride was added during 1 h. Then the mixture was boiled during 48 h. The acetone (ca. 500 mL) was partially removed on the rotary evaporator. 1.2 L 10% aq. Na$_2$CO$_3$ was added to the residue. After extraction with ethyl acetate (1×1 L+2×500 mL) the organic phase was washed with 1 L of a half-saturated NaCl solution. After drying over Na$_2$SO$_4$ and concentrating, the main part of the benzyl chloride was removed. 400 mL of pentane was added to the residue. The crystallisation began during stirring at 0° C. The crystals were separated and washed with 2×150 mL pentane and dried during 2 h at 15 mbar (40 C° bath temperature) and 2 h under high vacuum at room temperature to yield 230 g (75%) 4-benzyloxybromobenzene.

b) Preparation of 1-ethyl-1-methyl-4-oxo-piperidinium-iodide

To a solution of 93 g (730 mmol) 1-ethyl-4-piperidone (Aldrich 27950-1) in 730 mL acetone 124 g (876 mmol) methyl iodide (Acros 12237) was added during 30 min. The temperature was kept at 25–30° C. The product began to precipitate after addition of ⅓ of the methyl iodide. The mixture was stirred for 5 h at 22° C. and 30 min at 0° C. The cold suspension was filtered and the product was washed with acetone to yield 188 g (95%) 1-ethyl-1-methyl-4-oxo-piperidinium iodide.

c) Preparation of (R)-1-(1-phenyl-ethyl)-piperidin-4-one 84.6 g (698 mmol) of (R)-(+)-1-phenylethylamine (Merck no. 807031) and 1.4 L ethanol were mixed under argon. A solution of 203 g (1.47 mol) K$_2$CO$_3$ in water was added. The mixture was heated at 80° C. under stirring and a solution of 188 g (698 mmol) 1-ethyl-1-methyl-4-oxo-piperidinium iodide in 700 mL water was added during 1 h. The mixture was heated again for 105 min under stirring and then ethanol was removed on the rotary evaporator.

The residue was extracted with dichloromethane (1×1.5 L+1×1 L). The organic phases were washed with half-saturated NaCl solution (2×800 mL) and dried with Na$_2$SO$_4$. After evaporation of the solvent 144 g crude (R)-1-(1-phenyl-ethyl)-piperidin-4-one was obtained. 70 mL 37% HCl were added at 5° C. to 300 mL of isopropanol during 30 min. The mixture was added during 2 h under stirring at 15–20° C. to a solution of 144 g crude (R)-1-(1-phenyl-ethyl)-piperidin-4-one in 100 mL ethylacetate. Crystallisation began after addition of ⅓ of the above mixture. The suspension was stirred overnight at room temperature and then for 3 h at 0° C. After adding 80 mL of pentane the mixture was stirred again for 3 h at 0° C. The product was separated and washed with isopropanol (3×70 mL). After drying the hydrochloride (188 g) was suspended in 1 L dichloromethane and 700 mL of 10% Na$_2$CO$_3$ was added. The organic phase was separated and washed with half-saturated NaCl (1×1 L). After drying over MgSO$_4$ the organic phase was concentrated. The residue was dried over 2 h in high vacuum to yield 113 g (R)-1-(1-phenyl-ethyl)-piperidin-4-one.

d) Preparation of (R)-4-(4-benzyloxy-phenyl)-1-(1-phenyl-ethyl)-piperidin-4-ol 175.2 g (666 mmol) of 4-benzyloxybromobenzene was dissolved in 1.4 L dry THF (MS 4 A) under argon. The solution was cooled to −75° C. and a solution of 416 mL 1.6 M butyllithium (666 mmol) in hexane was added during 40 min. After stirring for 1 h a solution of 113 g (555 mmol) (R)-1-(1-phenyl-ethyl)-piperidin-4-one in 400 mL dry THF was added during 1 h at −75° C. The mixture was stirred for another 1 h and, after heating to room temperature, poured into 1.5 L of ice water. The mixture was extracted with 1 L ethyl acetate. The organic phase was washed with 1 L of a half-saturated NaCl solution, dried over Na$_2$SO$_4$ and concentrated to yield 262 g of (R)-4-(4-benzyloxy-phenyl)-1-(1-phenyl-ethyl)-piperidin-4-ol.

e) Preparation of (R)-4-(4-Benzyloxy-phenyl)-1-(1-phenyl-ethyl)-1,2,3,6 tetrahydropyridine 121.7 g crude (R)-4-(4-benzyloxy-phenyl)-1-(1-phenyl-ethyl)-piperidin-4-ol was dissolved at 40° C. in 1.21 L dichloroethane. 59.4 g (471 mmol) oxalic acid (Merck 492) was added. The mixture was boiled for 3 h, while 20 mL of water was separated. The reaction mixture was washed at room temperature with 1.2 L 10% Na$_2$CO$_3$. The precipitate (52 g) was separated from filtrate A and added to a mixture of 250 mL 2 N NaOH and 300 mL dichloromethane, where it was dissolved after stirring for 30 min at 30–35° C. The organic phase was separated and washed with a half-saturated NaCl solution. The resulting precipitate was separated and dissolved in 200 mL dichloromethane and 60 mL methanol. The combined organic phases were concentrated after drying over $Na_2SO_4$. 80 mL ethyl acetate was added to the residue and stirred for 2 h. The crystals were separated, washed with pentane, and dried to yield 36.5 g of (R)-4-(4-benzyloxy-phenyl)-1-(1-phenyl-ethyl)-1,2,3,6-tetrahydropyridine.

The organic phase of the above-mentioned filtrate A was washed with 1.5 L of a half-saturated NaCl solution. After drying the organic phase was concentrated. 80 mL ethyl acetate and 30 mL ether were added to the residue. After stirring for 3 h at 0° C., the crystals were separated and then washed with ethylacetate (2×20 mL) and pentane (50 mL) and dried to yield 33.0 g of (R)-4-(4-benzyloxy-phenyl)-1-(1-phenyl-ethyl)-1,2,3,6-tetrahydropyridine.

In total: 33.0 g+36.5 g=69.5 g (R)-4-(4-benzyloxy-phenyl)-1-(1-phenyl-ethyl)-1,2,3,6-tetrahydropyridine (73% based on (R)-1-(1-phenyl-ethyl)-piperidin-4-on) was obtained.

EXAMPLE 4

Preparation of Starting Material a) Preparation of 2-(4-benzyloxy-phenyl)-propen-2

At room temperature 29.6 g of methyltriphenylphosphonium bromide (83 mmol) was suspended in 75 mL of tetrahydrofuran. A solution of 9.2 g of potassium tert-butoxide (82 mmol) in 35 mL of tetrahydrofuran was added over 30 min, and the mixture was stirred for 10 min at room temperature and was then cooled to 0° C. At this temperature, a solution of 17.0 g of 4-benzyloxyacetophenone (75 mmol) in 100 mL of tetrahydrofuran was added during 1.5 h to the solution of the ylide. Stirring at 0° C. was continued for 1 h, then 1 mL of acetic acid was added to the reaction mixture. The reaction mixture was poured into a mixture of 300 mL of saturated aq. sodium bicarbonate, 200 g of ice and 250 mL of ethyl acetate. Then the aqueous phase was extracted with ethyl acetate. The organic phases were washed with 200 mL of 20% aq. sodium chloride, combined, dried ($Na_2SO_4$) and evaporated under reduced pressure to give 40.5 g of a white solid residue. The residue was suspended in 250 mL of hexane, and the mixture was stirred overnight at room temperature. The tripenylphosphinoxide was filtered off and washed with hexane. The filtrate was evaporated to give 15.8 g of a white solid. In order to remove traces of triphenylphosphine oxide, the product was passed through a pad of silica gel using hexane-ethyl acetate 95:5 (750 mL) as eluent. The combined fractions containing the desired compound were evaporated. The residue was suspended in 80 mL of pentane, then the product was collected by filtration, washed with pentane and dried to a constant weight resulting in 14.1 g 2-(4-benzyloxy-phenyl)-propen-2.

b) Preparation of (R)-4-(4-benzyloxy-phenyl)-1-(1-phenyl-ethyl)-1,2,3,6-tetrahydro-pyridine At room temperature 20.7 g of (R)-1-phenylethylamine hydrochloride (131 mmol) was dissolved in 60 mL of water. 22 mL of 36.5% aqueous formaldehyde was added and the mixture was stirred 10 min at room temperature and then warmed up to 40° C. At this temperature, a solution of 26.75 g of 2-(4-benzyloxy-phenyl)-propen-2 (119 mmol) in a mixture of 30 mL of dioxane and 74 mL of dichloromethane was continuously added over 1.25 h. During and after the addition of the olefin solution, dichloromethane was distilled off. After the removal of dichloromethane, the reaction mixture was stirred at 70° C. overnight. A solution of 9.96 g of conc. sulphuric acid (99 mmol) in 30 mL of water was added during 5 min to the reaction mixture which was then heated to 95–100° C. and stirred at this temperature for 5.5 h. The reaction mixture was slowly poured into a mixture of 250 mL of 10% aq. sodium carbonate and ice and then extracted with 600 mL of dichloromethane. The organic phases were extracted with one portion of 600 mL of 20% aq. sodium chloride, combined, dried ($Na_2SO_4$) and evaporated under reduced pressure to give 64 g crude product as a brown-red oil which partially crystallised. The crude product was dissolved in 250 mL of dichloromethane. 120 mL of isopropanol was added and the dichloromethane as well as a small part of the isopropanol was distilled off at reduced pressure (rotary evaporator, bath 45° C.). White crystals started to precipitate, and the suspension was stirred at 0° C. for 2 h. The crystals were collected on a filter funnel and washed with three portions of 50 mL of cold isopropanol and with 60 mL of hexane. After drying for 2 h at 16 mbar/50° C. and for 2 h at 0.2 mbar/22° C., 29.2 g (66%) (R)-4-(4-benzyloxy-phenyl)-1-(1-phenyl-ethyl)-1,2,3,6-tetrahydro-pyridine was obtained.

EXAMPLE 5

Preparation of Starting Material a) Preparation of 2-(4-benzyloxy-phenyl)-propan-2-ol The reaction flask was charged under argon with 3.45 g of magnesium (142 mmol). A solution of 21.16 g of methyl iodide (147 mmol) in 120 mL of tert-butyl-methyl-ether was added during 45 min at 45° C. under stirring. Then stirring was continued for 1 h at 45° C. and then a solution of 27.12 g of 4-benzyloxyacetophenone (120 mmol) in 100 mL of tetrahydrofuran was added during 45 min., while a temperature of 45° C. was again maintained. Stirring at 45° C. was continued for 1.5 h. After cooling to room temperature, the white suspension was poured into a mixture of 100 mL of 10% aqueous ammonium chloride and of ice and extracted with 150 mL of ethyl acetate. The aqueous phase was separated and extracted with 100 mL of ethyl acetate. The organic phase was washed with 120 mL of 20% aq. sodium chloride, combined, dried ($MgSO_4$) and evaporated under reduced pressure to give 29.9 g of crude product as an oil which partially crystallised. The crude product was taken up in 30 mL of dichloromethane. The solution was concentrated at the rotary evaporator almost to dryness. Then 6 mL of ethyl acetate was added followed by gradual addition of a total of 180 mL of hexane. The suspension was then kept at 0° C. for 30 min. The crystals were collected and washed with cold hexane. After drying for 2 h at 16 mbar/45° C., 26.7 g (92%) 2-(4-benzyloxy-phenyl)-propan-2-ol was obtained.

b) Preparation of (R)-4-(4-benzyloxy-phenyl)-1-(1-phenyl-ethyl)-1,2,3,6-tetrahydro-pyridine At room temperature 6.94 g of (R)-1-phenylethylamine hydrochloride (44 mmol) was dissolved in 24 mL of water. 8.0 g of 36.5% aqueous formaldehyde (2.92 g HCHO, 97 mmol) was added and the mixture was stirred for 10 min. Then, a solution of 9.68 g of 2-(4-benzyloxy-phenyl)-propan-2-ol (40 mmol) in 10 mL of dioxane was added. The reaction mixture was heated to 70° C. and stirred overnight at this temperature. A solution of 1.72 g of conc. sulphuric acid (17.6 mmol) in 8 ml of water was added to the reaction mixture within 5 min. Then the mixture was heated to 100° C. and stirred at this temperature for 7 h. The reaction mixture was slowly poured into a mixture of 150 mL of 10% aq. sodium carbonate and 50 g of ice and extracted with 450 mL of dichloromethane. The organic phases were extracted with 150 mL of water, combined, dried ($Na_2SO_4$) and evaporated under reduced pressure to give 18.1 g crude product as a orange-red oil which partially crystallised. The crude product was dissolved in 60 mL of dichloromethane. 80 mL of isopropanol was added and the dichloromethane as well as a small part of the isopropanol was distilled off at 400 mbar (rotary evaporator, bath 55° C.). White crystals precipitated, and the suspension was stirred 1 h at room temperature and additionally 1 h at 5° C. The crystals were collected and washed with 2 portions of 25 mL isopropanol and with 2 portions of 25 mL hexane. The product was then dried for 2 h at 16 mbar/40° C. and for 3 h at 0.2 mbar/22° C. to yield 9.1 g (61%) of (R)-4-(4-benzyloxy-phenyl)-1-(1-phenyl-ethyl)-1,2,3,6-tetrahydro-pyridine.

c) Preparation of (R)-1-phenylethylamin hydrochloride

At room temperature 122 g of (R)-1-phenylethylamine (1.0 mol) was dissolved in 30 mL of isopropanol. The solution was stirred and cooled to 0° C. Then, a previously prepared solution of 100 mL of 37% hydrochloric acid (118 g, 1.2 mol) in 320 mL of isopropanol was added during 1 h. The solution was stirred at 0° C. for an additional 40 min, and then it was concentrated on a rotary evaporator (16 mbar, bath 45° C.) to a volume of 300 mL. The translucent gel which had formed was transferred into a 1.5 l flask, then, under stirring, 250 mL of tert-butyl-methyl-ether was slowly added. Crystals started to form and the suspension was stirred at 0° C. for 3 h. The product was collected by filtration, washed with 100 mL of tert-butyl-methyl-ether and dried at 30° C./16 mbar for 4 hours to give 133 g (84%) of 1-phenylethylamine hydrochloride.

EXAMPLE 6

Preparation of Starting Material a) Preparation of methyl-4-benzyloxybenzoate

To a solution of 15.2 g of methyl-4-hydroxybenzoate (100 mmol) in 125 mL of N,N-dimethylformamide was added under stirring 33.13 g of potassium carbonate (240 mmol). Then 17.45 g of benzyl bromide (102 mmol) was added within 5 min. The mixture was stirred at 25° C. using a water bath. The reaction was complete after 3 h. The reaction mixture was poured into a mixture of 180 g of ice and 200 mL of ethyl acetate. After extraction, the aqueous phase was separated and extracted with three portions of 80 mL of ethyl acetate. The organic phase was washed with two portions of 150 mL of water, combined, dried (MgSO$_4$) and partially concentrated to give a thick suspension. 60 mL of pentane was added and the suspension was stirred during 2 h at room temperature. The crystalline methyl 4-benzyloxybenzoate was collected on a filter, washed with pentane and dried.

b) Preparation of 2-(4-benzyloxy-phenyl)-propan-2-ol

Under argon 6.63 g of magnesium (273 mmol) was suspended in 15 mL of tert-butyl methyl ether. A solution of 38.68 g of methyl iodide (273 mmol) in 145 mL of tert-butyl methyl ether was added during 45 min under stirring while maintaining the temperature at 40° C. Then stirring was continued at 40° C. for 1.5 h and then the mixture was cooled to room temperature. A solution of 30.0 g of methyl 4-benzyloxybenzoate (124 mmol) in 120 mL of tetrahydrofuran was then added during 1 h. The temperature was kept at 20° C. After complete addition, the reaction mixture was heated to 42° C. and stirred 3 h at this temperature. After cooling to room temperature, the reaction mixture was poured into a mixture of 300 mL of 10% aqueous ammonium chloride and 100 g of ice and extracted with ethyl acetate. The organic phases were washed with water and saturated aqueous sodium bicarbonate, combined, dried and evaporated to give the crude product as an oil which partially crystallised. The product was dissolved at 25° C. in diethyl ether. When crystals started to separate the solution was cooled to 18° C. After 30 min hexane was added. The suspension was then stirred for 1 h at 5° C. The crystalline 2-(4-benzyloxy-phenyl)-propan-2-ol was collected on a filter and washed with hexane.

c) Preparation of (R)-4-(4-benzyloxy-phenyl)-1-(1-phenyl-ethyl)-1,2,3,6-tetrahydro-pyridine At room temperature, the reaction flask was charged with 10.66 g of (R)-1-phenylethylamine (88 mmol) and 40 mL of water. Under stirring, the pH of the mixture was adjusted to a value of 4.1 by slow addition of aqueous hydrochloric acid. Then 16.0 g of 36.5% aqueous formaldehyde (5.84 g HCHO, 194 mmol) was added and the mixture was stirred for 10 min. A solution of 19.38 g of 2-(4-benzyloxy-phenyl)-propan-2-ol (80 mmol in 20 mL of dioxane) was then added. The reaction mixture was heated to 70° C. and stirred overnight at this temperature. A solution of 3.44 g of conc. sulphuric acid (35 mmol) in 16 mL of water was added during 5 min. to the reaction mixture which was then heated to 100° C. and stirred at this temperature for 7 h. The reaction mixture was slowly poured into a mixture of 300 mL of 10% aq. sodium carbonate and 100 g of ice and extracted with dichloromethane. The organic phases were extracted with water, combined, dried and evaporated to an orange-red oil which partially crystallised. The crude product was dissolved in 120 mL of dichloromethane. 160 mL of isopropanol was added and the dichloromethane as well as a part of the isopropanol was distilled off at 400 mbar (rotary evaporator, bath 55° C.). White crystals precipitated. The crystals were collected on a filter funnel and washed with isopropanol and then with hexane. The obtained (R)-4-(4-benzyloxy-phenyl)-1-(1-phenyl-ethyl)-1,2,3,6-tetrahydro-pyridine was then dried for 2 h at 16 mbar/40° C. and for 3 h at 0.2 mbar/22° C.

EXAMPLE 7

Preparation of a Precursor for Renin Inhibitors a) Preparation of (3R,4R)-4-(4-hydroxy-phenyl)-piperidin-3-ol-hydrochloride The reaction flask was charged under argon with 250 mg of 10% carbon-palladium (Degussa E-101 N/D), then a solution of 5 g (11.8 mmol) of (3R,4R)-4-(4-benzyloxy-phenyl)-1-((R)-1-phenyl-ethyl)-piperidin-3-ol hydrochloride in 50 mL of methanol and 5 mL water was added. After hydogenation during 6 h at room temperature and normal pressure the catalyst was separated by filtration and washed with methanol. The filtrate was concentrated and the remaining water was azeotropically removed at the rotary evaporator using toluene (3×100 mL) to give 2.7 g of (3R,4R)-4-(4-hydroxy-phenyl)-piperidin-3-ol hydrochloride as white crystals.

b) Preparation of (3R,4R)-3-hydroxy-4-(4-hydroxy-phenyl)-piperidin-1-carboxylic-acid-tert-butylester 2.5 g of (3R,4R)-4-(4-hydroxy-phenyl)-piperidin-3-ol hydrochloride was dissolved in 33 mL of methanol. Then 2.3 g of triethylamine was added and the mixture was cooled to −18° C. A solution of 2.6 g (11.9 mmol) di-tert.-butyl-dicarbonate in 16 mL of methanol was added during 30 min. The reaction mixture was stirred for 1 h at −18° C. and then heated slowly to 0° C. After stirring for additional 2 h at 0° C. 10 mL of water was added and the methanol was removed with the rotary evaporator. The residue was dissolved in a mixture of dichloromethane/water and a solution of 10% NaHSO$_4$ was slowly added. After extraction the organic phase was washed with a NaHCO$_3$ solution and with a half-saturated NaCl solution. The water phase was extracted twice with dichloromethane. The crude product was obtained after drying (MgSO$_4$) and concentrating the organic phases. Then diethylether was added and the product started to crystallise. After adding pentane the mixture was placed in the refrigerator. The next day the crystals were separated, washed with pentane and dried into vacuo yielding 3.1 g of (3R,4R)-3-hydroxy-4-(4-hydroxy-phenyl)-piperidin-1-carboxylic-acid-tert-butylester as white crystals.

EXAMPLE 8

Preparation of 1-[2-[7-[(3R,4R)-4-[4-[3-(2-methoxy-benzyloxy)-propoxy]-phenyl]-piperidin-3-yloxymethyl]-naphthalen-2-yloxy]-ethyl]-4-methyl-piperazine a) A solution of 16.50 g (56.24 mmol) of (3R,4R)-3-hydroxy-4-(4-hydroxy-phenyl)-piperidine-1-carboxylic acid tert-butylester in 40 ml of dimethylformamide was treated in succession with 12.68 g (59.06 mmol) of 1-(3-chloro-propoxymethyl)-2-methoxy-benzene (WO 97/09311) and 12.44 g (89.99 mmol) of potassium carbonate. This mixture was stirred at 120° C. for 26 hours. Subsequently, it was filtered, concentrated to a few milliliters, poured into 300 ml of an ice/water mixture and extracted three times with 100 ml of methylene chloride each time. The combined organic phases were washed once with a small amount of water, dried over magnesium sulphate, evaporated under reduced pressure and dried in a high vacuum. The resulting crude product (31.64 g) was separated on silica gel using a 99:1 mixture of methylene chloride and methanol as the eluent and yielded 25.4 g (95.8% of theory) (3R,4R)-3-hydroxy-4-[4-[3-(2-methoxy-benzyloxy)-propoxy]-phenyl]-piperidine-1-carboxylic acid tert-butylester as a slightly yellow oil; MS: 489 (M+NH$_4$+).

b) 25.4 g (53.86 mmol) of (3R,4R)-3-hydroxy-4-[4-[3-(2-methoxy-benzyloxy)-propoxy]-phenyl]-piperidine-1-carboxylic acid tert-butylester and 17.78 g (55.06 mmol) of 2-chloromethyl-7-(2-trimethylsilanyl-ethoxymethoxy)-naphthalene (WO 97/09311) were dissolved in 180 ml of dimethylformamide under argon and then 2.49 g (57.09 mmol) of sodium hydride dispersion (55% in mineral oil) was added. Subsequently, the mixture was stirred at room temperature for 5 hours. The reaction mixture was poured onto ice-water, the product was extracted 3 times with methylene chloride, the organic phases were washed twice with distilled water, then dried over magnesium sulphate, filtered and concentrated in a water-jet vacuum. The resulting crude product was chromatographed on silica gel with methylene chloride and methanol to give 36.43 g (89.2% of theory) of (3R,4R)-4-[4-[3-(2-methoxy-benzyloxy)-propoxy]-phenyl]-3-[7-(2-trimethylsilanyl-ethoxymethoxy)-naphthalen-2-ylmethoxy]-piperidine-1-carboxylic acid tert-butylester as a yellowish oil; MS: 759 (M+H)+.

c) 36.43 g (48.06 mmol) of (3R,4R)-4-[4-[3-(2-methoxy-benzyloxy)-propoxy]-phenyl]-3-[7-(2-trimethylsilanyl-ethoxymethoxy)-naphthalen-2-ylmethoxy]-piperidine-1-carboxylic acid tert-butylester was placed in 700 ml of abs. methanol at 0° C., then 48 ml (96.1 mmol) of hydrochloric acid in methanol (2.0 molar) was added dropwise at 5° C. max. and thereafter the mixture was warmed to room temperature. After 120 minutes the reaction mixture was poured into ice-cold sodium hydrogen carbonate solution and the product was extracted three times with methylene chloride. The organic phases were washed once with distilled water, then dried over magnesium sulphate, filtered and concentrated in a water-jet vacuum. The resulting crude product was chromatographed on silica gel with methylene chloride and methanol yielding 28.06 g (93% of theory) (3R,4R)-3-(7-hydroxy-naphthalen-2-yloxymethyl)-4-[4-[3-(2-methoxy-benzyloxy)-propoxy]-phenyl]-piperidine-1-carboxylic acid tert-butylester as a light yellow amorphous solid; MS: 645 (M+NH$_4$+).

d) A mixture of 10.15 g (16.17 mmol) of (3R,4R)-3-(7-hydroxy-naphthalen-2-yloxymethyl)-4-[4-[3-(2-methoxy-benzyloxy)-propoxy]-phenyl]-piperidine-1-carboxylic acid tert-butylester, 2.80 g (19.42 mmol) of 1-(2-hydroxy-ethyl)-4-methyl-piperazine [J. Pharm. Sci. (1968), 57(3), 384–9] and 5.51 g (21.01 mmol) of triphenylphosphine were dissolved in 450 ml of tetrahydrofuran. Then, a solution of 4.75 g (20.22 mmol) of di-tert-butyl azodicarboxylate in 50 ml of tetrahydrofuran was slowly added to the reaction mixture at 0° C. and stirring continued for 2 hours at room temperature. The reaction mixture was concentrated in a water-jet vacuum. The resulting crude product was chromatographed on silica gel with methylene chloride and methanol yielding 9.18 g (75.3% of theory) of (3R,4R)-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidine-1-carboxylic acid tert-butylester as a colourless oil; MS: 754 (M+H)+.

e) A solution of 9.15 g (12.14 mmol) (3R,4R)-4-[4-[3-(2-methoxy-benzyloxy)-propoxy]-phenyl]-3-[7-[2-(4-methyl-piperazin-1-yl)-ethoxy]-naphthalen-2-ylmethoxy]-piperidine-1-carboxylic acid tert-butylester in 250 ml of methanol was treated at room temperature with 36.41 ml of a 2.0 M solution of hydrogen chloride in methanol and the mixture was stirred at 50° C. for 4 hours. Subsequently, the solution was evaporated under reduced pressure and the residue was partitioned between 200 ml of saturated sodium carbonate solution and 150 ml of methylene chloride. The aqueous phase was again extracted twice with 100 ml of methylene chloride; thereafter the organic phases were combined, dried over sodium sulphate and evaporated under reduced pressure. For purification, the crude product was chromatographed on silica gel using a 90:10 mixture of methylene chloride and methanol as the eluent resulting in 5.25 g (66% of theory) of 1-[2-[7-[(3R,4R)-4-[4-[3-(2-methoxy-benzyloxy)-propoxy]-phenyl]-piperidin-3-yloxymethyl]-naphthalen-2-yloxy]-ethyl]-4-methyl-piperazine as an amorphous, colourless solid; MS: 654 (M+H)+.

EXAMPLE 9

Preparation of (3R,4R)-4-[4-[3-(2-methoxy-benzyloxy)-propoxy]-phenyl]-3-(1,2,3,4-tetrahydro-quinolin-7-ylmethoxy)-piperidine a) 3.40 g (7.20 mmol) of (3R,4R)-3-hydroxy-4-[4-[3-(2-methoxy-benzyloxy)-propoxy]-phenyl]-piperidine-1-carboxylic acid tert-butylester and 2.18 g (7.20 mmol) of 7-bromomethyl-quinoline hydrobromide (1:1) [J. Am. Chem. Soc. 77, 1054(1955)], were dissolved in 50 ml of absolute dimethylformamide under argon and then 0.83 g (19.0 mmol) of sodium hydride dispersion (55% in mineral oil) was added at room temperature in small portions. Subsequently, the mixture was stirred at room temperature for 16 hours. The reaction mixture was poured onto ice-water, the product was extracted 3 times with ethyl acetate, the combined organic phases were washed twice with distilled water, then dried over magnesium sulphate, filtered and concentrated. The crude product (5.2 g, yellow oil) was chromatographed on silica gel with ethyl acetate/hexane 2:1 to yield 3.77 g (85.4% of theory) of (3R,4R)-4-[4-[3-(2-methoxy-benzyloxy)-propoxy]-phenyl]-3-(quinolin-7-yl-methoxy)-piperidine-1-carboxylic acid tert-butylester as a colourless oil; MS: 613 (M+H)+.

b) 3.77 g (6.15 mmol) of (3R,4R)-4-[4-[3-(2-methoxy-benzyloxy)-propoxy]-phenyl]-3-(quinolin-7-yl-methoxy)-piperidine-1-carboxylic acid tert-butylester and 0.93 g (3.12 mmol) of nickel(II) chloride hexahydrate were dissolved in 50 ml of methanol. 0.93 g (24.8 mmol) of sodium borohydride was added at 0° C. in small portions over a period of 30 minutes. The resulting black suspension was then stirred for 1 hour at 0° C., and 2 hours at room temperature. The reaction mixture was slowly poured into a vigorously stirred mixture of 150 ml 5% ammonium chloride solution and 400 ml of ether. After further stirring for 30 minutes, the organic phase was separated. The slightly blue aqueous phase was further extracted 5 times with ether. The combined organic phases were washed twice with distilled water, then dried over magnesium sulphate, filtered and concentrated. The crude product (3.2 g, yellow oil) was chromatographed on silica gel with ethyl acetate/hexane 1:1 to yield 2.92 g (76.9% of theory) of (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester as a colourless oil; MS: 617 (M+H)$^+$.

c) 2.92 g (4.73 mmol) of (3R,4R)-4-[4-[3-(2-methoxy-benzyloxy)-phenyl]-3-(1,2,3,4-tetrahydro-quinolin-7-ylmethoxy)-piperidine-1-carboxylic acid tert-butylester were dissolved in 63 ml of abs. methanol, then 63 ml (126 mmol) of hydrochloric acid in methanol (2.0 molar) were added at room temperature. After stirring for 150 minutes at 50° C., the reaction mixture was poured into 150 ml ice-cold 5% sodium hydrogen carbonate solution and the product was extracted five times with 100 ml methylene chloride. The combined organic phases were washed twice with 50 ml distilled water, dried over magnesium sulphate, filtered and concentrated. The crude product (2.9 g, yellow oil) was chromatographed on silica gel with methylene chloride/methanol/28%ammonium hydroxide solution 14:1:0.1 v/v/v to yield 1.90 g (77.7% of theory) of (3R,4R)-4-[4-[3-(2-methoxy-benzyloxy)-propoxy]-phenyl]-3-(1,2,3,4-tetrahydro-quinolin-7-ylmethoxy)-piperidine as a slightly yellow resin; MS: 517 (M+H)$^+$.

What is claimed is:

1. A compound having the formula

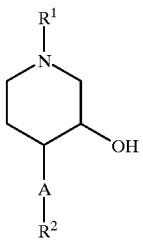

1 wherein
A is arylene;
R$^1$ is —C*R$^3$R$^4$R$^5$;
R$^2$ is —O-alkyl, —O-cycloalkyl, —O-alkenyl, —O-aryl, —O-aralkyl, —O-aralkoxyalkyl, —O-alkylsulfonyl, —O-arylsulfonyl;
R$^3$ is hydrogen;
R$^4$ is aryl;
R$^5$ is alkyl, cycloalkyl, aryl, alkoxyalkyl or hydroxyalkyl; and
C* is an asymmetric carbon atom; and
salts of said compound.

2. The compound of claim 1 wherein R$^5$ is alkyl or cycloalkyl.

3. The compound of claim 1 wherein R$^4$ is phenyl which optionally may be substituted by one or more groups independently selected from the group consisting of alkyl, halogen and nitro.

4. The compound of claim 1 wherein R$^4$ is phenyl and R$^5$ is methyl.

5. The compound of claim 1 wherein A is phenylene which optionally may be substituted by one to four substituents independently selected from the group consisting of alkyl, halogen and nitro.

6. The compound of claim 1 wherein R$^2$ is selected from the group consisting of —O-benzyl and —O-methyl.

7. A process for the preparation of a compound of formula 1, or a salt thereof,
comprising:

a) hydroboration of a compound of formula 2

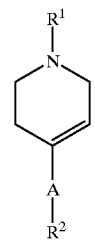

2 wherein,
A is arylene;
R$^1$ is —C*R$^3$R$^4$R$^5$;
R$^2$ is —O-alkyl, —O-cycloalkyl, —O-alkenyl, —O-aryl, —O-aralkyl, —O-aralkoxyalkyl, —O-alkylsulfonyl, —O-arylsulfonyl;
R$^3$ is hydrogen;
R$^4$ is aryl;
R$^5$ is alkyl, cycloalkyl, aryl, alkoxyalkyl or hydroxyalkyl; and
C* is an asymmetric carbon atom.

8. The process of claim 7 further comprising the step of isolating a desired stereoisomer.

9. The process of claim 8, wherein the desired stereoisomer is isolated by crystallisation of a salt of a compound of formula 1.

10. The process of claim 7 followed by a reaction with hydrogen.

11. The process of claim 7 wherein R$^5$ is alkyl or cycloalkyl.

12. The process of claim 7 wherein R$^4$ is phenyl which optionally may be substituted by one or more groups independently selected from alkyl, halogen or nitro.

13. The process of claim 7 wherein R$^4$ is phenyl and R$^5$ is methyl.

14. The process of claim 7 wherein A is phenylene which optionally may be substituted by one to four substituents each of which is independently selected from the group consisting of alkyl, halogen and nitro.

15. The process of claim 7 wherein R$^2$ is —O-benzyl or —O-methyl.

16. The process of claim 7 wherein a compound of the formula 2 is reacted with NaBH$_4$/BF$_3$.Et$_2$O, BH$_3$-THF or isopinocampheyl borane.

* * * * *